United States Patent
Chou (10) Patent No.: US 11,047,839 B2
(45) Date of Patent: Jun. 29, 2021

(54) SMART SENSING NETWORK

(71) Applicant: TricornTech Taiwan, Taipei (TW)

(72) Inventor: Tsung-Kuan A. Chou, San Jose, CA (US)

(73) Assignee: TRICORNTECH TAIWAN, Taipei (TW)

( * ) Notice: Subject to any disclaimer, the term of this patent is extended or adjusted under 35 U.S.C. 154(b) by 505 days.

(21) Appl. No.: 15/810,409

(22) Filed: Nov. 13, 2017

(65) Prior Publication Data

US 2018/0136180 A1    May 17, 2018

Related U.S. Application Data (60) Provisional application No. 62/423,033, filed on Nov. 16, 2016.

(51) Int. Cl.
*G01N 33/00*    (2006.01)

(52) U.S. Cl.
CPC ..... *G01N 33/0006* (2013.01); *G01N 33/0036* (2013.01)

(58) Field of Classification Search
CPC .................. G01N 33/0006; G01N 33/0036
USPC .............................................. 73/31.01, 31.02
See application file for complete search history.

(56) References Cited

U.S. PATENT DOCUMENTS

| | | | |
|---|---|---|---|
| 6,701,772 B2* | 3/2004 | Kreichauf | G08B 21/12 |
| | | | 73/23.2 |
| 7,360,461 B2* | 4/2008 | Desrochers | G01N 1/22 |
| | | | 73/863.71 |
| 8,190,367 B2* | 5/2012 | Bassa | B60H 1/00771 |
| | | | 702/3 |

(Continued)

FOREIGN PATENT DOCUMENTS

| TW | 201229441 A | 7/2012 |
|---|---|---|
| TW | 201337262 A | 9/2013 |
| TW | 201502508 A | 1/2015 |

OTHER PUBLICATIONS

Hasenfratz et al., "On-the-fly Calibration of Low-cost Gas Sensors", Computer Engineering and Networks Laboratory, ETH Zurich, Switzerland, Oct. 26, 2015, 16 pages.

(Continued)

*Primary Examiner* — Daniel S Larkin
(74) *Attorney, Agent, or Firm* — Womble Bond Dickinson (US) LLP (57) ABSTRACT

Embodiments are described of a sensing network including one or more sensor nodes, wherein each of the one or more sensor nodes includes a gas sensor that can measure the presence, concentration, or both, of one or more airborne pollutants in a nodal coverage area surrounding the sensor node. A sensor base that can measure the presence, concentration, or both, of one or more airborne pollutants is positioned in the nodal coverage area of each of the one or more sensor nodes, wherein the sensor base includes a gas sensor with higher accuracy, higher sensitivity, or both, than the gas sensors of the one or more sensor nodes. One or more servers communicatively coupled to the sensor base and the one or more sensors nodes. The sensor base and the sensor nodes can communicate their measurements to the server and the measurements of the sensor base are used by the server as a reference to correct the measurements of the one or more sensor nodes.

32 Claims, 9 Drawing Sheets

(56) References Cited

U.S. PATENT DOCUMENTS

| | | | | |
|---|---|---|---|---|
| 8,717,161 | B1* | 5/2014 | Gary | G08B 25/08 340/501 |
| 2013/0074575 | A1 | 3/2013 | Duric et al. | |
| 2013/0278427 | A1 | 10/2013 | Setton | |
| 2014/0238107 | A1 | 8/2014 | Chou et al. | |
| 2014/0278186 | A1* | 9/2014 | Herzl | G01N 33/0006 702/104 |
| 2015/0153299 | A1* | 6/2015 | Chou | G01N 33/0075 205/775 |
| 2015/0253300 | A1 | 9/2015 | Zanfei et al. | |
| 2015/0325100 | A1 | 11/2015 | Hunter et al. | |
| 2016/0123947 | A1 | 5/2016 | Bryant et al. | |

OTHER PUBLICATIONS

International Preliminary Report on Patentability received for PCT Patent Application No. PCT/US2017/061605, dated May 31, 2019, 10 pages.

International Search Report and Written Opinion received for PCT Patent Application No. PCT/US2017/061605, dated Feb. 9, 2018, 16 pages.

Office Action received for Taiwanese Patent Application No. 106139699, dated Jul. 9, 2019, 7 pages (3 pages of English Translation and 4 pages of Office Action).

Office Action received for Taiwanese Patent Application No. 106139699, dated May 20, 2020, 8 pages (4 pages of English Translation and 4 pages of Office Action).

Office Action received for Taiwanese Patent Application No. 106139699, dated Oct. 18, 2018, 15 pages (6 pages of English Translation and 9 pages of Office Action).

Supplementary European Search Report and Search Opinion received for EP Application No. 17871447.3, dated Sep. 7, 2020, 6 pages.

Office Action received for European Patent Application No. 17871447.3, dated Apr. 30, 2021, 3 pages.

Office Action received for Taiwanese Patent Application No. 109111005, dated Apr. 19, 2021, 11 pages (5 pages of English Translation and 6 pages of Office Action).

* cited by examiner

SMART SENSING NETWORK

CROSS-REFERENCE TO RELATED APPLICATIONS

This application claims priority under 35 U.S.C. § 119(e) to U.S. Provisional App. No. 62/423,033, filed 16 Nov. 2016, which is hereby incorporated by reference in its entirety.

TECHNICAL FIELD

The disclosed embodiments relate generally to air pollution sensing and monitoring and in particular, but not exclusively, to a smart sensing network for air pollution sensing and monitoring.

BACKGROUND

Air pollution within cities and industrial parks has worsened with modernization, and public health effects caused by air pollutants (e.g., chemicals, such as PM2.5, NOx, SOx, O3, and volatile organic compounds (VOCs)) have begun to gain increasing attention. Due to complex pollution sources, it is necessary to obtain denser spatial air quality monitoring data to provide the general public with updated air quality information at locations of interest.

Ambient air quality monitoring has been implemented, but because expensive and bulky lab instruments must be used to obtain reliable monitoring data, only a limited number of monitoring stations can be set up and installed at limited locations. And because the monitoring stations usually require large spaces for instrument setup (especially with gas chromatography instruments) they are mostly installed in suburban areas where there is room to accommodate them, with very few stations installed in cities where there is less room. As a result there is a need for using small, low-cost sensors to form a network to monitor spatial air quality across the city, which has become popular.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION OF THE ILLUSTRATED EMBODIMENTS

Embodiments are described of an apparatus, system and method for a smart sensing network for air pollution sensing and monitoring. Specific details are described to provide an understanding of the embodiments, but one skilled in the relevant art will recognize that the invention can be practiced without one or more of the described details or with other methods, components, materials, etc. In some instances, well-known structures, materials, or operations are not shown or described in detail but are nonetheless encompassed within the scope of the invention.

Reference throughout this specification to "one embodiment" or "an embodiment" means that a described feature, structure, or characteristic can be included in at least one described embodiment, so that appearances of "in one embodiment" or "in an embodiment" do not necessarily all refer to the same embodiment. Furthermore, the particular features, structures, or characteristics may be combined in any suitable manner in one or more embodiments.

Figure 1:
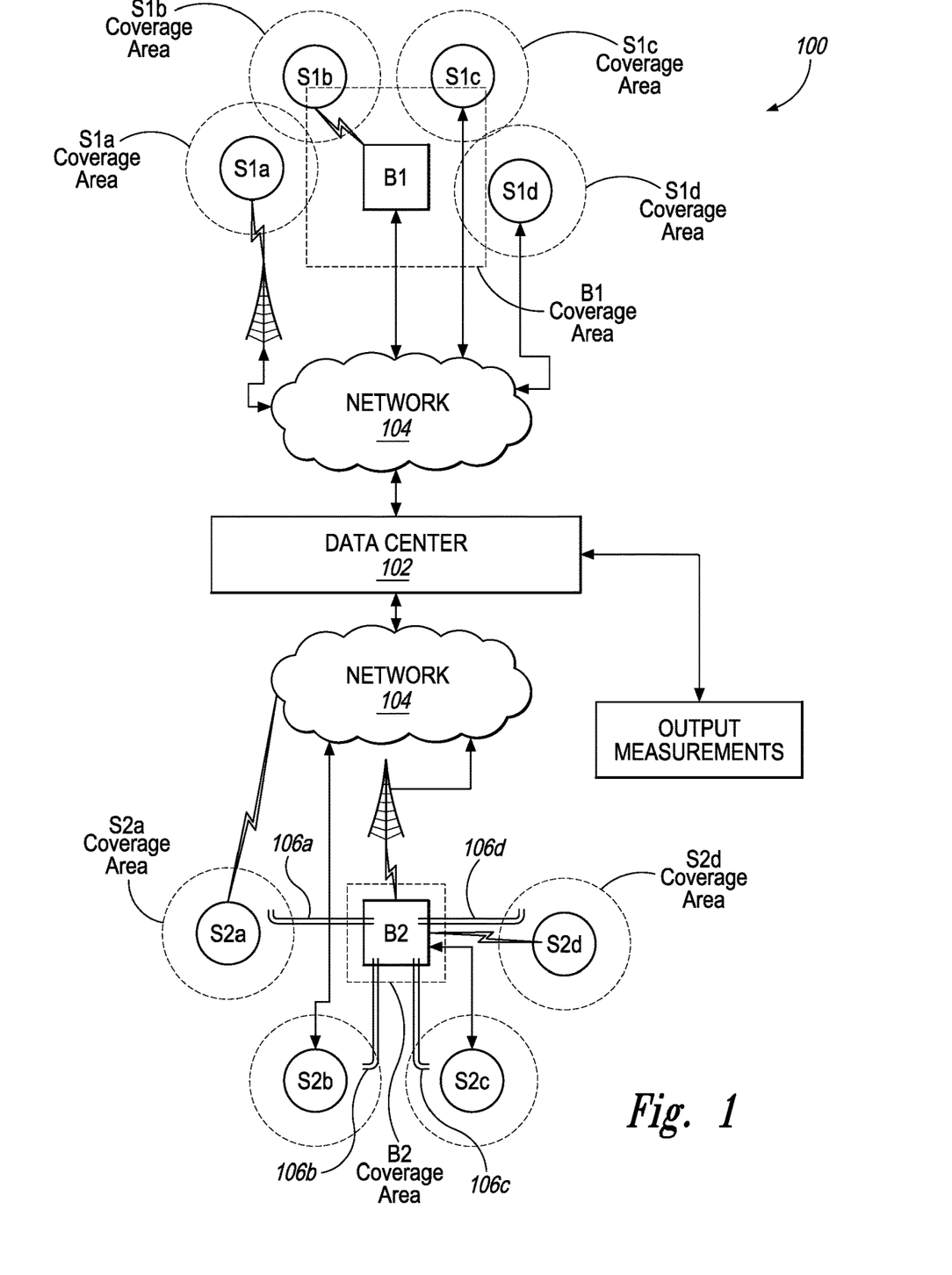
FIG. 1 is a block diagram of an embodiment of a smart pollution sensing and monitoring system.

FIG. 1 illustrates an embodiment of a smart air pollution sensing and monitoring system 100. System 100 includes a data center 102 communicatively coupled to one or more sensor bases B (i.e., B1 and B2 in the illustrated embodiment) and one or more sensor nodes S (i.e., S1$a$-S1$d$ and S2$a$-S2$d$ in the illustrated embodiment). The illustrated embodiment has two sensor bases B1-B2 and eight sensor nodes S1$a$-S1$d$ and S2$a$-S2$d$, but other embodiments can have more or less sensor bases than shown and more or less sensor nodes than shown.

Data center 102 includes various hardware elements, such as a communication interface, one or more servers each including at least one microprocessor, memory, and storage, and additional storage space that can include one or more databases, for instance to register information about the sensor bases B and sensor nodes S including their type, identity, location if fixed or current location if mobile, measurement history, etc. The communication interface communicatively couples data center 102 to sensor nodes S1$a$-S1$d$ and S2$a$-S2$d$ and sensor bases B1 and B2. Sensor nodes S1$a$-S1$d$ and S2$a$-S2$d$ and sensor bases B1-B2 can communicate with data center 102 by wire, wirelessly, or by some combination of wirelessly and wired. For instance, in the illustrated embodiment sensor nodes S1$a$ and S1$b$ communicate with data center 102 wirelessly via network 104, while sensor nodes S1$c$ and S1$d$ communicate with data center 102 by wire, also via a network 104. Similarly, sensor base B1 communicates with data center 102 by wire via network 104. Sensor base B2 communicates with data center 102 wirelessly via network 104, while sensor nodes S2$a$ and S2$d$ communicate with data center 102 wirelessly and sensor nodes S2$b$ and S2$c$ communicate with data center 102 via wire, both via network 104. Network 104 can be the Internet, or can be a local area network (LAN), a wide area network (WAN), or some other type of network in different embodiments.

Sensor nodes S1$a$-S1$d$ and S2$a$-S2$d$ are divided into sets that correspond to a sensor base: in the illustrated embodiment, sensor nodes S1$a$-S1$d$ are grouped with sensor base B1 and sensor nodes S2$a$-S2$d$ are grouped with sensor base B2, so that in each grouping there is a many-to-one correspondence between sensor nodes and sensor bases. Other embodiments need not have this many-to-one correspondence, but can instead have a one-to-one correspondence between sensor nodes and sensor bases. And although in the illustrated embodiment sensor bases B1-B2 are each grouped with four sensor nodes, in other embodiments each sensor base need not be grouped with the same number of sensor nodes.

Each sensor node S has a corresponding coverage area, which is an area in which an air sample gathered for analysis by the sensor node can be considered representative. Each sensor base B similarly has a corresponding coverage area. In the illustrated embodiment sensor base B1 has a coverage area that overlaps with the coverage areas of sensor nodes S1a-S1d, so that an air sample gathered for analysis by sensor base B1 can also be considered representative of conditions in the coverage areas of S1a-S1d. Sensor base B2, on the other hand, has a coverage area that does not overlap with the coverage areas of its set of sensor nodes S2a-S2d. In an embodiment where B2 is mobile, it can be moved into and out of the coverage areas of sensor nodes S2a-S2d. But in embodiments where B2 is stationary, for sensor base B2 to be able to collect air samples in the coverage areas of sensors S2a-S2d, a sampling manifold 106 includes one or more sampling tubes 106a-106d fluidly coupled to sensor base B2, with each sampling tube having one end at sensor base B2 and the other extended into the coverage areas of sensor nodes S2a-S2d. In the context of this application, "fluidly coupled" means coupled in such a way that fluid can flow one or both ways between two locations.

In some embodiments of system 100, sensor nodes S and sensor bases B occupy fixed positions and are thus fixed relative to each other. But as discussed below, in some embodiments at least one of sensor bases B1 and B2 can be mobile; in these embodiments the positions of sensor bases B relative to sensor nodes S can change, so that each sensor node need not be permanently assigned to a particular sensor base. As a result, the exact composition of a group—that is, the numbers and identities of sensor bases and the numbers and identities of corresponding sensor nodes—can change over time. In some embodiments with mobile sensor bases the changes can be frequent enough that no particular group is recognizable.

In the illustrated embodiment, sensor nodes S1a-S1d and S2a-S2d are fixed on-site low-cost air quality monitoring sensors, which are substantially less expensive than sensor bases B and can be easily deployed on-site at various locations to form a high-density sensing network for on-site monitoring and provide big data analysis to deliver time-dense and spatially-dense usable air quality information to the public about airborne pollutants. Airborne pollutants can include airborne chemicals and other airborne contaminants such as, without limitation, organic or inorganic chemicals such as volatile organic compounds (VOCs), NOx, SOx, O3; airborne particulate matter (PM), such as PM2.5 (i.e., particulate matter with 2.5 μm diameter) and PM10; compounds; heavy metal contaminants; airborne biological contaminants; etc.

The sensing data from sensor nodes can be wired or wirelessly uploaded to one or more servers for further data correction or analysis. In another embodiment, there can be a wired or wireless connection between sensor nodes S and sensor bases B; for instance, in the illustrated embodiment sensor node S1b can communicate wirelessly with sensor base B1, sensor node S2d can communicate wirelessly with sensor base B2, and sensor node S2c can communicate by wire with sensor base B2. In embodiments where sensor nodes S can communicate directly with sensor bases B, instead of transmitting sensor node data directly to data center 102, sensor nodes S can transmit sensor node data to data center 102 indirectly via a sensor base B. The low-cost sensors can provide real time or more frequent on-site air quality monitoring results. The low-cost sensors used for sensing nodes S can suffer from sensitivity drift, which requires periodic baseline/sensitivity drift check and correction.

Sensor bases B1-B2 serve as data references for their corresponding sensor nodes S. Sensor bases B1-B2 include analyzers to collect air samples and provide accurate, high-quality, and consistent measured results with high specificity on individual compound detection. Sensor bases B1-B2 measure air quality at specific locations and times using a high-performance air quality analyzer that can collect air samples and analyze them to provide concentrations of airborne pollutants. Pollutants measured can include, without limitation, organic or inorganic chemicals, such as volatile organic compounds (VOCs), NOx, SOx, O3; airborne particulate matter (PM) such as PM2.5 (i.e., particulate matter with 2.5 μm diameter) and PM10; compounds; heavy metal contaminants; airborne biological contaminants; etc. Sensor bases B1-B2 can be fixed or mobile; when mobile, sensor bases B can include a position sensor, such as a GPS receiver, which they can use to report their current location to data center 102. The sensor data for measurements carried out by sensor bases B1-B2 can be uploaded, by wire or wirelessly, to one or more servers in data center 102. The sensor base data can then be used as reference for data correction on sensor node results. Each sensor base can also provide periodic reference data for on-site sensor node data correction, recalibration, or replacement.

Figure 2A:
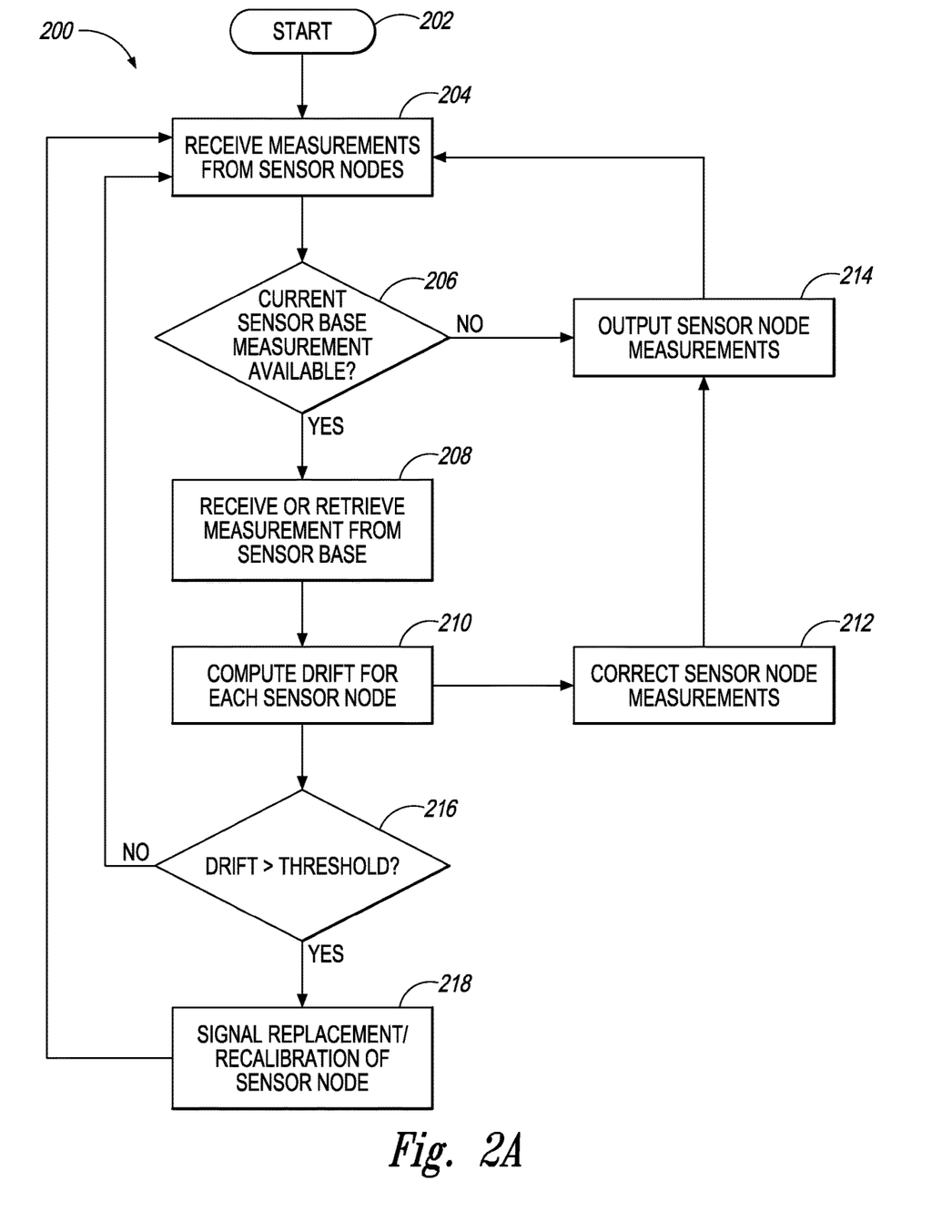
FIGS. 2A-2B are a flowchart and a pair of graphs, respectively, illustrating an embodiment of a process for correcting measurements received from sensor nodes.
Figure 2B:
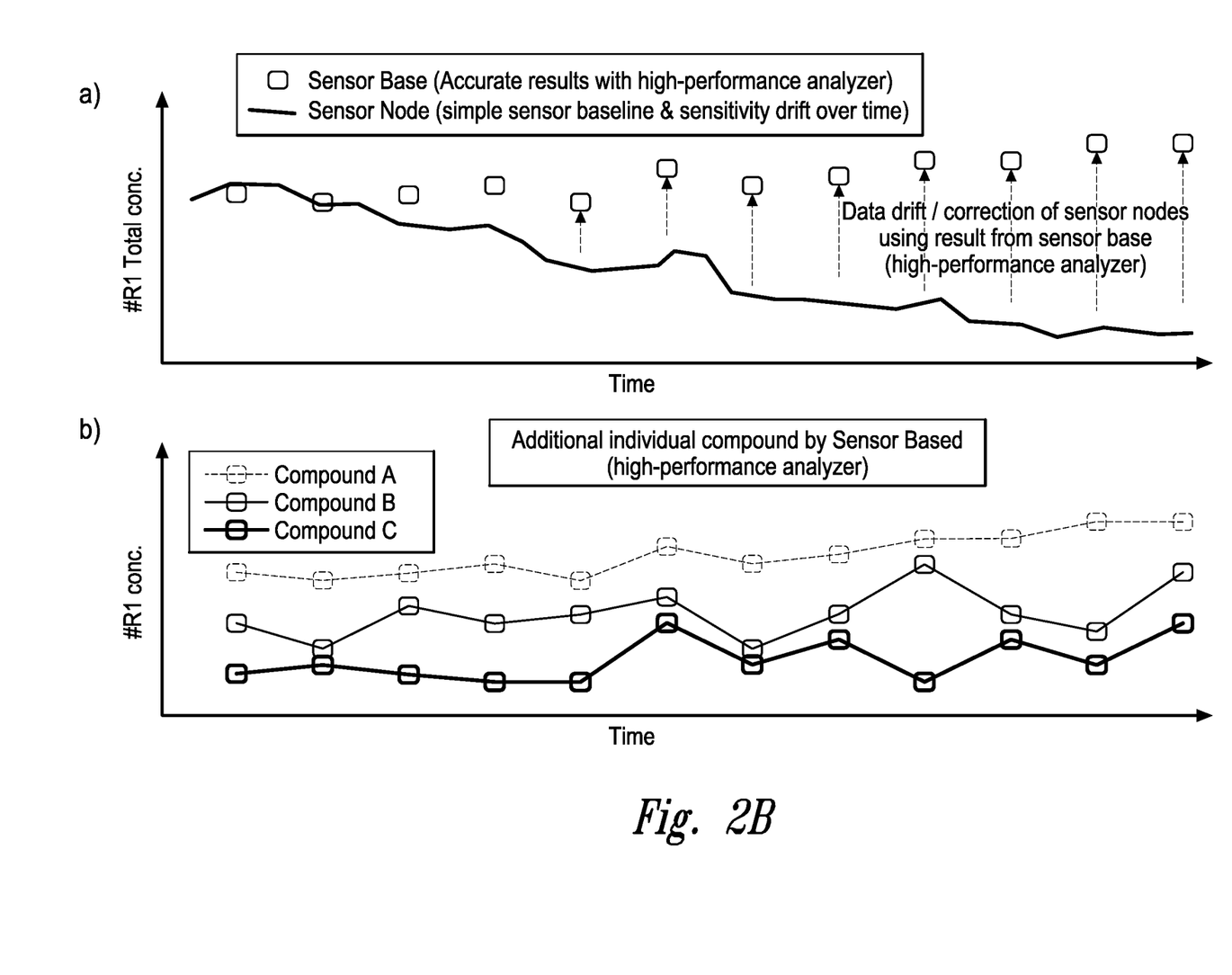

FIGS. 2A-2B together illustrate an embodiment of a process 200 by which measurements from the sensor bases B can be used to correct measurements from sensor nodes S. FIG. 2A is a flowchart that will be discussed below n in the context of system 100 and the graphs of FIG. 2B. In system 100 the process 200 is carried out primarily by data center 102.

The process starts at block 202. A block 204, data center 102 receives measurements from one or more sensor nodes with which it can communicate. At block 206 the process checks whether a current sensor base measurement is available for that sensor—that is, whether there is a sensor base measurement that is close in both time and space to the received sensor node measurements. In an embodiment in which sensor base B and sensor nodes S are fixed relative to each other, the sensor base measurement will essentially always be current. But in embodiments in which sensor bases B are not fixed relative to the sensor nodes—embodiments in which sensor bases B are mobile, for instance—the sensor base measurement may not be current if the sensor base has not recently been in the neighborhood of a sensor node from which a measurement has been received. In one embodiment sensor base B can collect and analyze air samples at or around the nodal coverage area of each sensor node S at a specified fixed frequency, but in other embodiments sensor base B can collect and analyze air samples at a special temporal period. In some embodiments special temporal periods include at random or when needed. In still other embodiments, if the data center determines that a specific sensor node is starting to drift faster than expected but still functions acceptably before replacement, the corresponding sensor base (fixed or mobile) that covers the sensor node can be adjusted to increase air sample monitoring frequency around that sensor node to provide more accurate data correction.

If at block 206 there is no current sensor base data available, the process proceeds to block 214, where the sensor node data is reported. At block 214 the sensor node data can be reported as is—i.e., with whatever drift is present in the data. Alternatively, in the absence of current base sensor data, before the final data is reported the data server can utilize advanced artificial intelligence analysis to predict a possible correction based on the previous time-progressing drift/degradation of the same sensor node.

If in block 206 a current sensor base measurement is available, then the process moves to block 208, where it receives a current measurement from a sensor base or retrieves a current measurement from a database, and then proceeds to block 210 where it computes a drift for each received sensor node measurement. In one embodiment, the drift can be defined as the difference between the sensor node measurement and the sensor base measurement at or near a particular spatial location and a particular time, as shown in FIG. 2B. As seen in the upper graph (a) of FIG. 2B, the sensor nodes have data drift while continuing their air sensing (sensing concentration drooping down as shown in the figure). Without the data correction, the result from sensor node will provide the wrong monitoring result by misleading reduction of pollutant concentration. But with the additional accurate data from the sensor base's high-performance analyzer (mobile or stationary), the drifted results of the sensor node are corrected based on the sensor base result measured at substantially the same time and substantially the same location (although the sensor base data might not provide more discrete monitoring in time for each sensor node). Drifts can be computed for measurements of total pollutant concentrations, for concentrations of individual compounds, or both. For instance, in a sensor node S that can sense five different pollutants, there can be a single drift for the total pollutant concentration, there can be five separate drifts, one for each pollutant, or there can be both total and individual drifts.

Having computed a drift for each sensor node measurement at block 210, the process proceeds to block 212 where the sensor node measurements are corrected. After the sensor node data correction using the sensor base result, the data drift issue of the low-cost sensor node can be more accurately obtained as shown in the lower graph (b) of FIG. 2B. With such a method, hundreds or thousands of sensor node data can be corrected and achieve reliable sensing network results. The process then proceeds to block 214, where the sensor node measurements are output to a user for further analysis or information. The process then returns to block 204 where it can receive further measurements from sensor nodes.

Having computed a drift for each sensor node at block 210, in addition to moving to block 212 the process can also move to block 216, were it checks whether the computed drift is greater than some threshold that indicates that a sensor node must be replaced or recalibrated. If at block 216 the drift of a particular sensor node is greater than some set threshold, the process moves on to block 218, where it signals to a user that replacement or recalibration of the sensor node is required. After block 218, the process returns to block 204 to receive measurements from the same or other sensor nodes. But if at block 216 the drift of a particular sensor node is less than some set threshold, the process returns to block 204 to receive measurements from the same or other sensor nodes.

Figure 3:
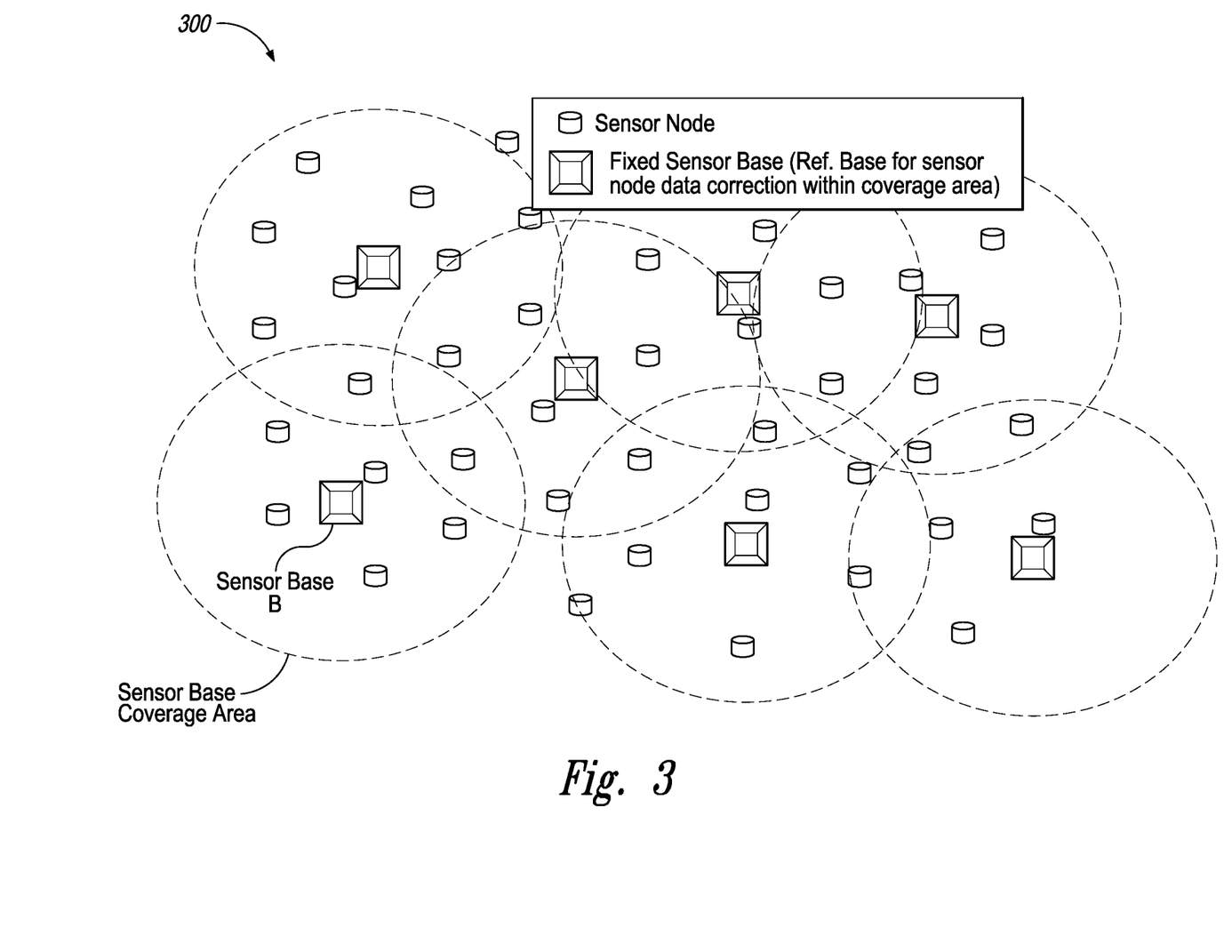
FIG. 3 is a block diagram of another embodiment of a smart pollution sensing and monitoring system.

FIG. 3 illustrates an embodiment of positioning sensor bases and sensor nodes in an air quality monitoring system 300. In system 300, the sensor nodes S and sensor bases B are fixed in space relative to each other, are stationary, and are deployed at various spatial locations. The coverage area of each sensor base B encompasses one or more sensor nodes S, such that the coverage areas of each sensor base and its corresponding sensor nodes overlap. Each sensor base can provide reference data for corresponding sensor nodes in the sensor base coverage area.

Figure 4:
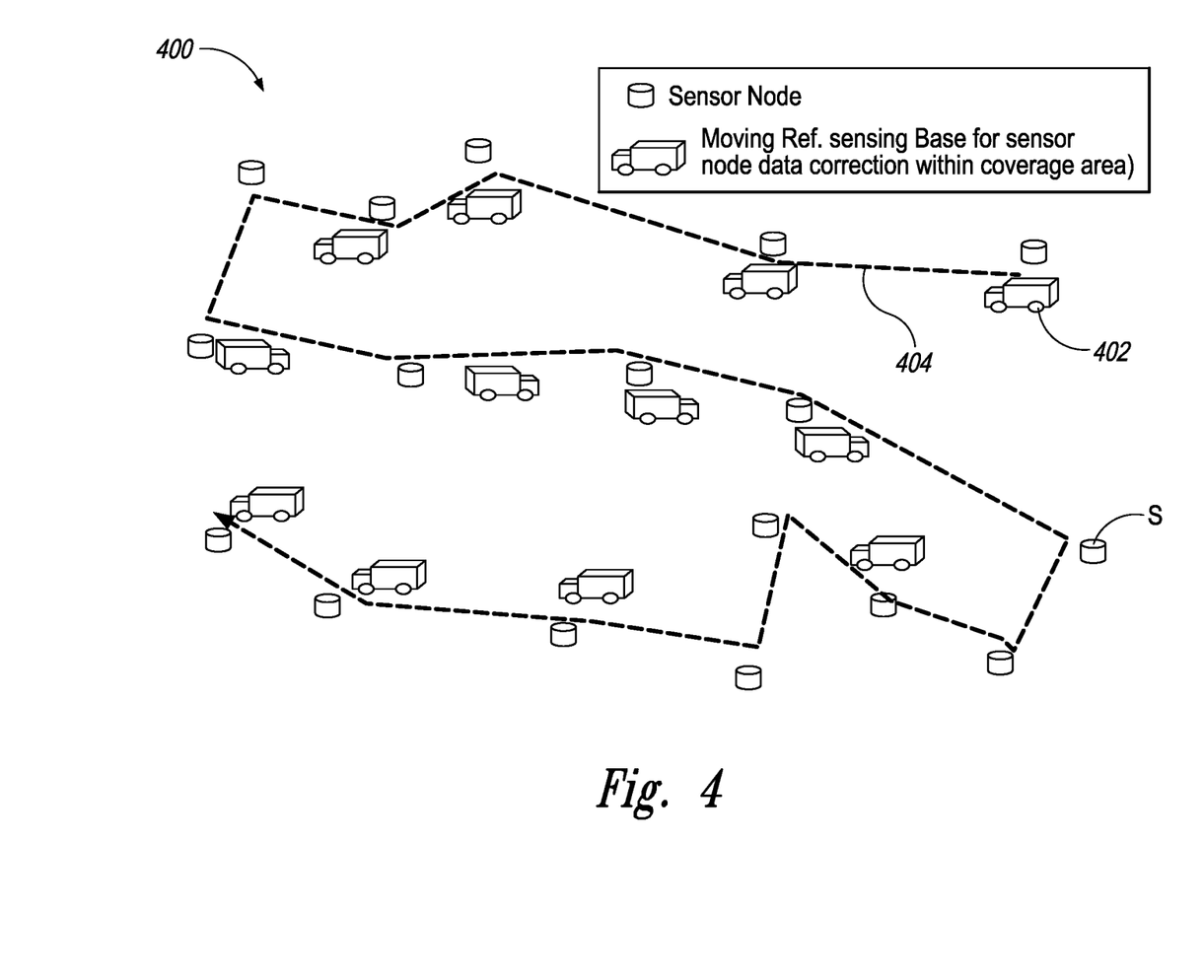
FIG. 4 is a block diagram of another embodiment of a smart pollution sensing and monitoring system.

FIG. 4 illustrates another embodiment of positioning of sensor bases and sensor nodes in an air quality monitoring system 400. In system 400 the sensor nodes S are deployed at various spatial locations. A mobile sensor base 402 travels along a path 404 that brings it near enough to each sensor node S to allow it to collect a sample at or near the location where each sensor node is installed and analyze the collected samples. Using a mobile sensor base B allows a small number of sensor bases to cover a larger number of sensor nodes S, so that spatially dense reference data can be obtained for data correction of each sensor node.

Figure 5:
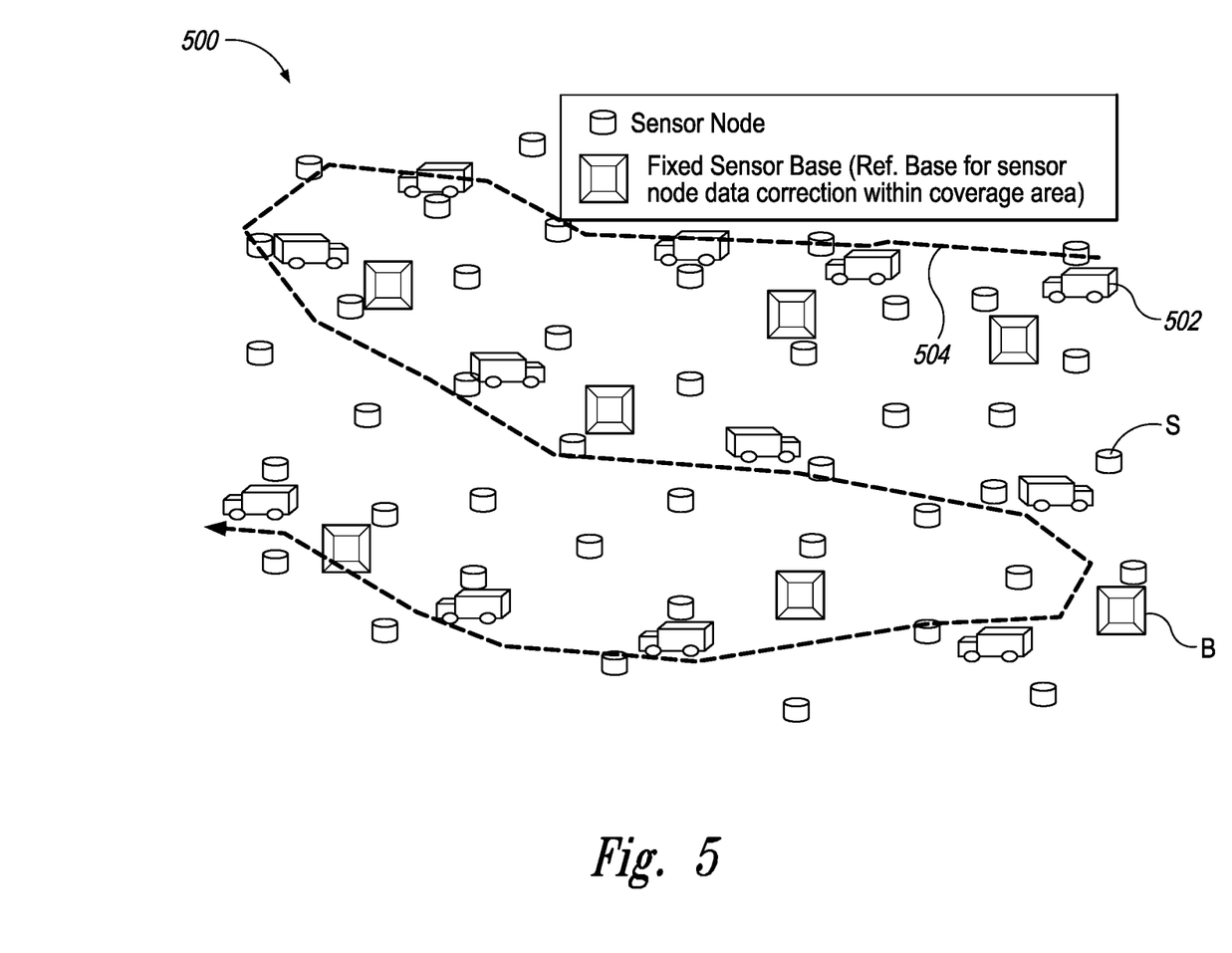
FIG. 5 is a block diagram of another embodiment of a smart pollution sensing and monitoring system.

FIG. 5 illustrates another embodiment of positioning sensor bases and sensor nodes in an air quality monitoring system 500. In system 500 a series of stationary sensor bases B and various sensor nodes S are deployed at various spatial locations. A mobile sensor base 502 travels along a path 504 that allows it to collect samples at or near the location where each sensor base B and each sensor node S is installed and analyze the collected samples. By doing so, mobile sensor base 502 serves as a backup to the multiple fixed sensor bases B and also collects and provides reference data for data correction of each sensor node. In some extreme cases, some sensor nodes S may be installed at locations where they are not covered by any fixed sensor bases B. The mobile sensor base can be used to provide the reference data for drift correction needed on those sensor nodes.

Figure 6:
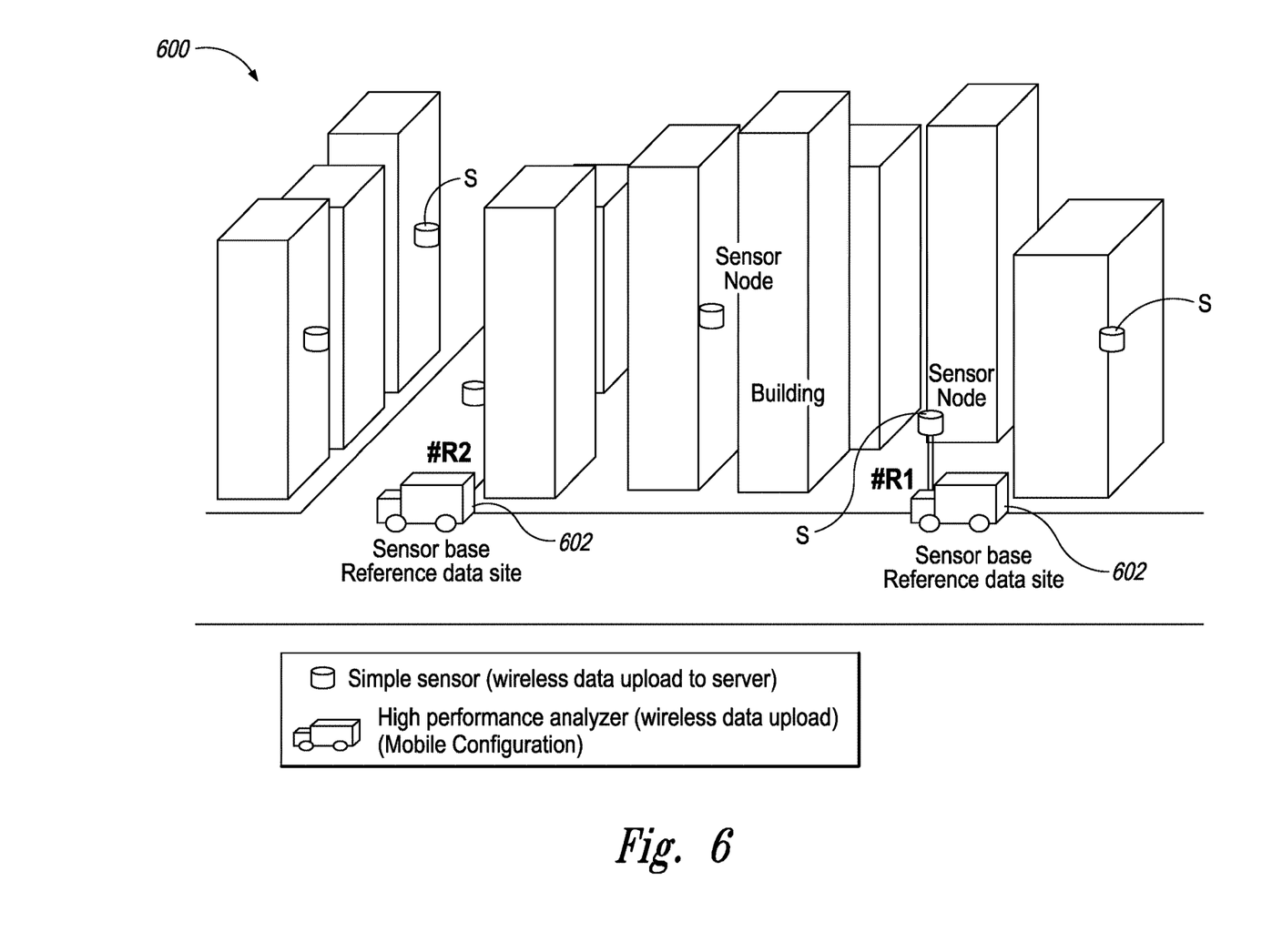
FIG. 6 is a block diagram of another embodiment of a smart pollution sensing and monitoring system.

FIG. 6 illustrates another embodiment of positioning sensor bases and sensor nodes in an air quality monitoring system 600. FIG. 6 illustrates low-cost sensor nodes S deployed in a city, primarily outside of a building, in the streets, and on the sidewalks, to form a sensing network to monitor urban air quality. Mobile sensor bases 602, which can for instance be sensor bases installed on vehicles for mobile monitoring, can drive through city streets near known locations of sensor nodes S to collect reference data when the sensor base moves to corresponding nearby sensing nodes.

Figure 7:
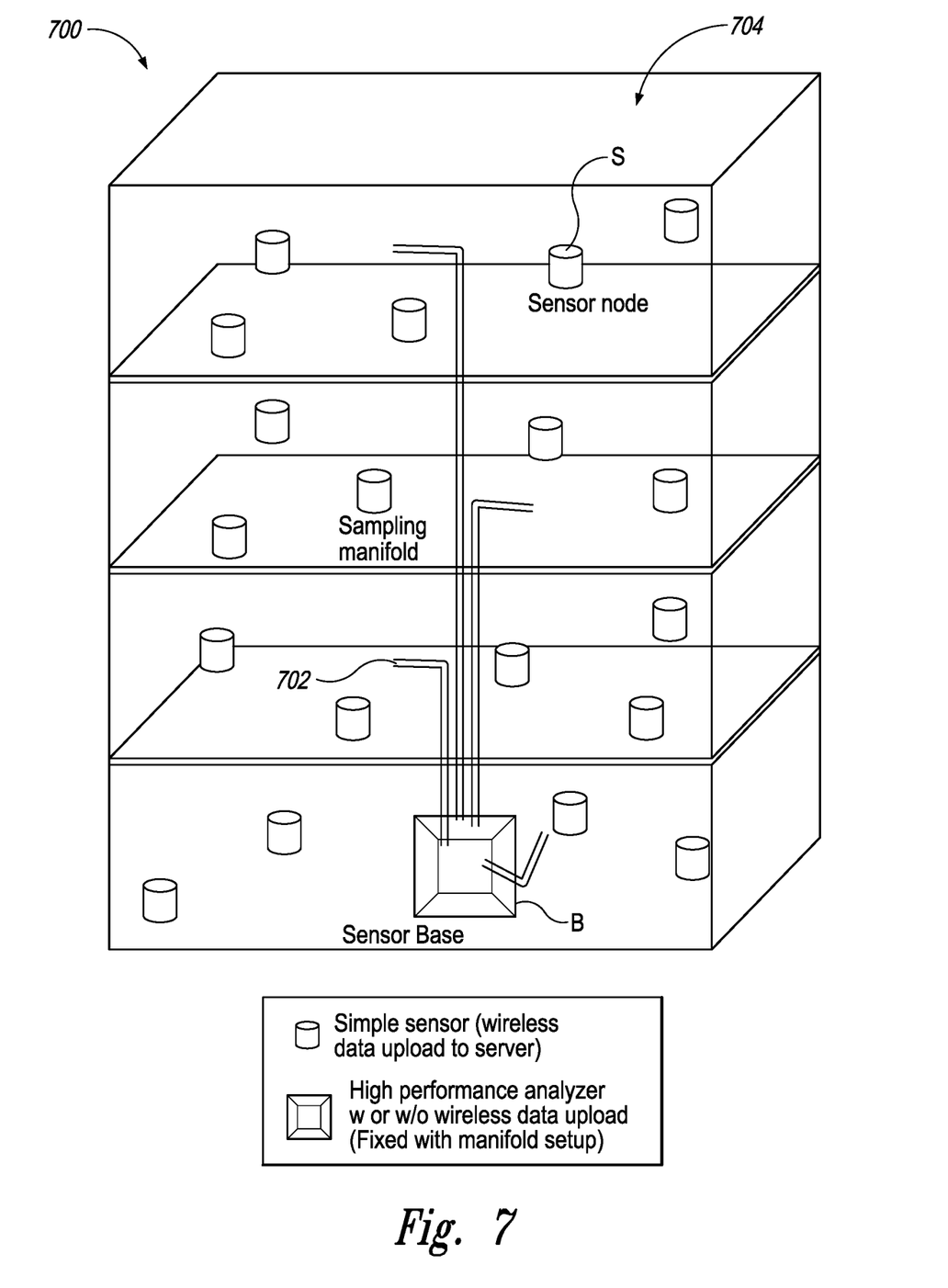
FIG. 7 is a block diagram of another embodiment of a smart pollution sensing and monitoring system.

FIG. 7 illustrates another embodiment of positioning sensor bases and sensor nodes in an air quality monitoring system 700. FIG. 7 illustrates low-cost sensor nodes S deployed inside a building 704 with a high-performance analyzer serving as sensor base B. Manifold tubes or pipes 702 are extended from sensor base B to different floors and locations for air quality monitoring in the interior of the building. The sensor base data for each floor/location can be used to correct the sensor node data.

Figure 8:
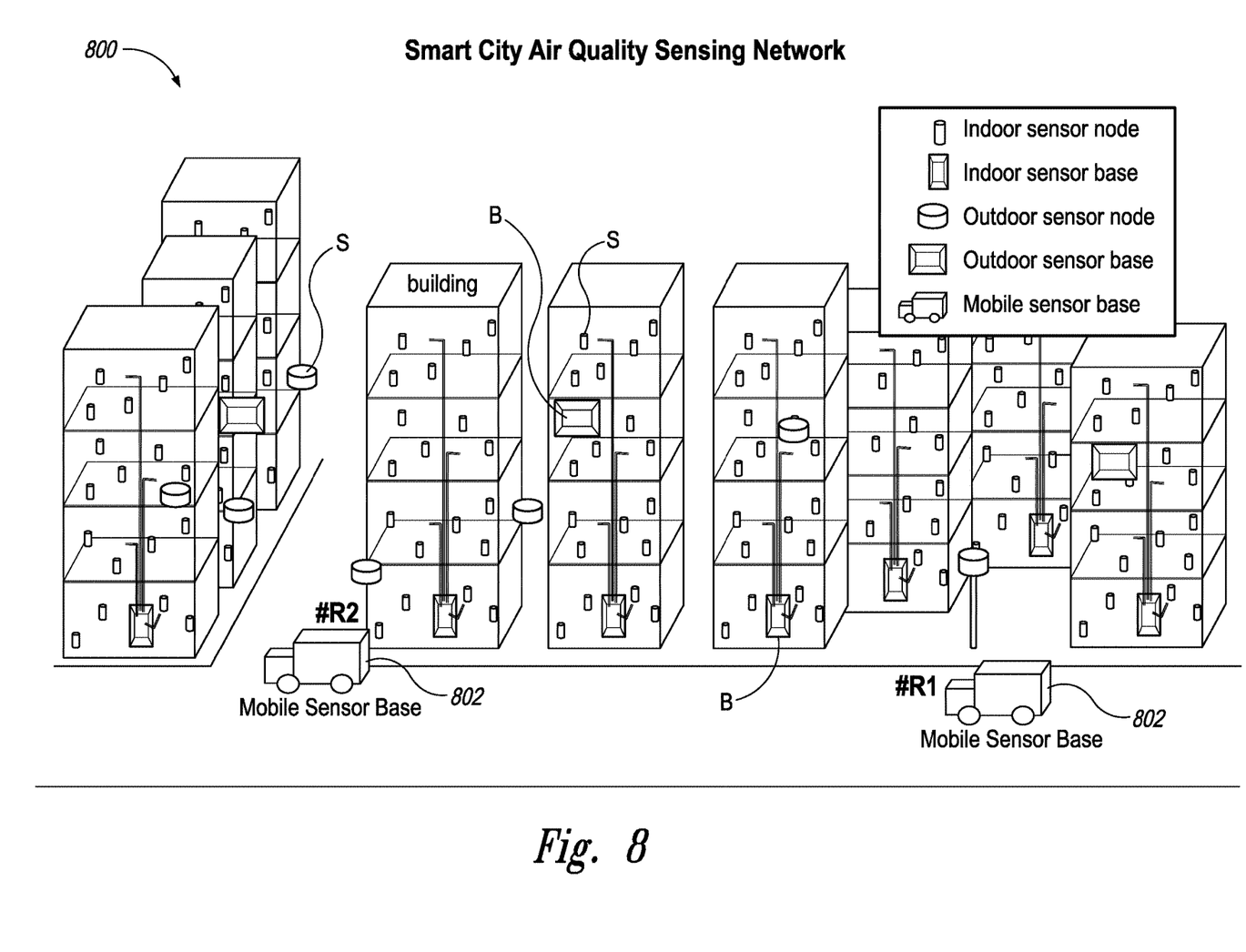
FIG. 8 is a block diagram of another embodiment of a smart pollution sensing and monitoring system.

FIG. 8 illustrates another embodiment of positioning sensor bases and sensor nodes in an air quality monitoring system 800. Sensor nodes S are installed at various locations inside and outside buildings in a city (although the embodiment is not limited to a city). Stationary sensor bases B can be, but aren't necessarily, installed inside or outside the building, with or without manifold sampling connected to air of interest from the stationary base station. Additional mobile sensor bases 802 can be used to transport the high-performance air quality analyzers to corresponding sensor node locations, which can cover sensor nodes positioned at locations the stationary sensor bases cannot reach for monitoring.

The above description of embodiments, including what is described in the abstract, is not intended to be exhaustive or to limit the invention to the described forms. Specific embodiments of, and examples for, the invention are described herein for illustrative purposes, but various equivalent modifications are possible within the scope of the invention in light of the above detailed description, as those skilled in the relevant art will recognize.

The invention claimed is:

1. A sensing network comprising:
   one or more sensor nodes, wherein each of the one or more sensor nodes includes a gas sensor that can measure the presence, concentration, or both, of one or more airborne pollutants in a nodal coverage area surrounding the one or more sensor nodes;
   a sensor base that can measure the presence, concentration, or both, of the one or more airborne pollutants in the nodal coverage area of each of the one or more sensor nodes, wherein the sensor base includes a gas sensor with higher accuracy and higher sensitivity than the gas sensors of the one or more sensor nodes; and
   one or more servers communicatively coupled to the sensor base and the one or more sensors nodes;
   wherein the sensor base and the one or more sensor nodes can communicate their measurements to the one or more servers and wherein the measurements of the sensor base are used by the one or more servers as a reference to correct the measurements of the one or more sensor nodes.

2. The sensing network of claim 1 wherein the sensor base collects air samples at or around the nodal coverage area of each sensor node.

3. The sensing network of claim 2 wherein the sensor base is fixed and has one or more sampling tubes through which it can collect samples from the nodal coverage area of each sensor node.

4. The sensing network of claim 2 wherein the sensor base is fixed and can collect air samples in a base coverage area surrounding the sensor base, and wherein the base coverage area encompasses the nodal coverage areas of the one or more sensor nodes so that a sample collected by the sensor base can be considered representative of conditions in the nodal coverage areas of each of the one or more sensor nodes.

5. The sensing network of claim 2 wherein the sensor base is mobile and can be moved into and out of the nodal coverage areas of each the one or more sensor nodes to collect samples from the nodal coverage areas.

6. The sensing network of claim 1 wherein the measurements received from the sensor base are used to recalibrate the one or more sensor nodes.

7. The sensing network of claim 1 wherein the sensor base and the one or more sensor nodes can be communicatively coupled to the one or more servers wirelessly, by wire, or both.

8. The sensing network of claim 7 wherein the one or more sensor nodes can be communicatively coupled to the sensor base wirelessly, by wire, or both.

9. The sensing network of claim 8 wherein the one or more sensor nodes can be communicatively coupled to the one or more servers via the sensor base.

10. The sensing network of claim 1 wherein the sensor base collects air samples at or around the nodal coverage area of each sensor node at a specified fixed frequency or special temporal period.

11. The sensing network of claim 10 wherein the sensor base collects air samples at or around the nodal coverage area of each sensor node at a frequency or temporal duration that depends on a drift rate of the one or more sensor nodes.

12. The sensing network of claim 1 wherein correcting the measurements of the one or more sensing nodes comprises:
    computing a drift for each sensing node, the drift being computed based on the difference between the measurement of a particular pollutant by each sensor node and the measurement of the particular pollutant by the sensor base; and
    adjusting the measurements obtained for the particular pollutant from each sensor node based on the drift computed for the particular pollutant at each sensing node.

13. The sensing network of claim 1 wherein correcting the measurements of the one or more sensing nodes comprises:
    computing a drift for each sensing node, the drift being computed based on the difference between the measurement of a total concentration of pollutants by each sensor node and the measurement of the total concentration of pollutants by the sensor base; and
    adjusting the measurements obtained for the total concentration of pollutants from each sensor node based on the drift computed for the total concentration of pollutants at each sensing node.

14. The sensing network of claim 1 wherein correcting the measurements of the one or more sensing nodes comprises:
    computing a separate drift for each pollutant sensed at each sensing node, each drift being computed based on the difference between the measurement of a concentration of each pollutants by each sensor node and the measurement of the concentration of each pollutants by the sensor base; and
    adjusting the measurements obtained for the concentration of each pollutant from each sensor node based on the drift computed for each pollutant.

15. The sensing network of claim 1 wherein the one or more airborne pollutants are organic or inorganic chemicals, airborne particulate matter (PM), heavy metal contaminants, or airborne biological contaminants.

16. The apparatus of claim 1 wherein the gas sensors of the one or more sensor nodes are a different type of sensor than the gas sensor of the sensor base.

17. A process comprising:
    transmitting a measurement from one or more sensor nodes to one or more servers communicatively coupled to the one or more sensors nodes, wherein each of the one or more sensor nodes includes a gas sensor that can measure the presence, concentration, or both, of one or more airborne pollutants in a nodal coverage area surrounding the one or more sensor nodes;
    transmitting a measurement from a sensor base to the one or more servers, wherein the sensor base is communicatively coupled to the one or more servers, wherein the sensor base can measure the presence, concentration, or both, of the one or more airborne pollutants in the nodal coverage area of each of the one or more sensor nodes, and wherein the sensor base includes a gas sensor with higher accuracy and higher sensitivity, or both, than the gas sensors in the one or more sensor nodes; and
    correcting the measurements from the one or more sensor nodes using the measurements received from the sensor base.

18. The process of claim 17 wherein the sensor base collects air samples at or around the nodal coverage area of each sensor node.

19. The process of claim 18 wherein the sensor base is fixed and has one or more sampling tubes through which it can collect samples from the nodal coverage area of each sensor node.

20. The process of claim 18 wherein the sensor base is fixed and can collect air samples in a base coverage area surrounding the sensor base, and wherein the base coverage area encompasses the nodal coverage areas of the one or more sensor nodes so that a sample collected by the sensor base can be considered representative of conditions in the nodal coverage areas of each of the one or more sensor nodes.

21. The process of claim 18 wherein the sensor base is mobile and can be moved into and out of the nodal coverage areas of each the one or more sensor nodes to collect samples from the nodal coverage areas.

22. The process of claim 17 wherein the measurements received from the sensor base are used to recalibrate the one or more sensor nodes.

23. The process of claim 17 wherein the sensor base and the one or more sensor nodes can be communicatively coupled to the one or more servers wirelessly, by wire, or both.

24. The process of claim 23 wherein the one or more sensor nodes can be communicatively coupled to the sensor base wirelessly, by wire, or both.

25. The process of claim 24 wherein the one or more sensor nodes can be communicatively coupled to the data center via the sensor base.

26. The process of claim 17 wherein the base node collects air samples at or around the nodal coverage area of each sensor node at a specified fixed frequency.

27. The process of claim 17 wherein the sensor base collects air samples at or around the nodal coverage area of each sensor node at a frequency or specific temporal period that depends on a drift rate of the one or more sensor nodes.

28. The process of claim 17 wherein correcting the measurements of the one or more sensing nodes comprises:
   computing a drift for each sensing node, the drift being computed based on the difference between the measurement of a particular pollutant by each sensor node and the measurement of the particular pollutant by the sensor base; and
   adjusting the measurements obtained for the particular pollutant from each sensor node based on the drift computed for the particular pollutant at each sensing node.

29. The process of claim 17 wherein correcting the measurements of the one or more sensing nodes comprises:
   computing a drift for each sensing node, the drift being computed based on the difference between the measurement of a total concentration of pollutants by each sensor node and the measurement of the total concentration of pollutants by the sensor base; and
   adjusting the measurements obtained for the total concentration of pollutants from each sensor node based on the drift computed for the total concentration of pollutants at each sensing node.

30. The process of claim 17 wherein correcting the measurements of the one or more sensing nodes comprises:
   computing a separate drift for each pollutant sensed at each sensing node, each drift being computed based on the difference between the measurement of a concentration of each pollutants by each sensor node and the measurement of the concentration of each pollutants by the sensor base; and
   adjusting the measurements obtained for the concentration of each pollutant from each sensor node based on the drift computed for each pollutant.

31. The process of claim 17 wherein the one or more airborne pollutants are organic or inorganic chemicals, airborne particulate matter (PM), heavy metal contaminants, or airborne biological contaminants.

32. The process of claim 17 wherein the gas sensors of the one or more sensor nodes are a different type of sensor than the gas sensor of the sensor base.

* * * * *